US00PP36131P2

(12) United States Plant Patent
Bédard

(10) Patent No.: US PP36,131 P2
(45) Date of Patent: Sep. 24, 2024

(54) GRANDIFLORA ROSE PLANT NAMED 'WEKsecjuc'

(50) Latin Name: *Rosa hybrida*
Varietal Denomination: WEKsecjuc

(71) Applicant: Early Morning LLC, Lawrenceburg, IN (US)

(72) Inventor: Christian Bédard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/390,244

(22) Filed: Dec. 20, 2023

(51) Int. Cl.
*A01H 5/02* (2018.01)
*A01H 6/74* (2018.01)

(52) U.S. Cl.
USPC ..... Plt./134

(58) Field of Classification Search
USPC ..... Plt./101, 130, 134
See application file for complete search history.

(56) References Cited

U.S. PATENT DOCUMENTS

PP8,494 P 12/1993 Tracy
PP18,473 P2 2/2008 Carruth

OTHER PUBLICATIONS

Bedard, C., "Shrub Rose Plant Named "Wekblufstow"," U.S. Appl. No. 18/533,666, filed Dec. 8, 2023, 13 pages.
Carruth, T., "Grandiflora Rose Plant Named "Wekalmylcas"," U.S. Appl. No. 18/540,248, filed Dec. 14, 2023, 11 pages.
Carruth, T., "Hybrid Tea Rose Plant Named "Wekmotonton"," U.S. Appl. No. 18/541,817, filed Dec. 15, 2023, 11 pages.
Make Me Blush TM, "Weeks Roses," 2024 Wholesale Rose Catalog, 2024, 100 pages.

*Primary Examiner* — Susan McCormick Ewoldt
(74) *Attorney, Agent, or Firm* — McKee, Voorhees & Sease, PLC

(57) ABSTRACT

A new variety of Grandiflora rose suitable for garden decoration, having flowers of yellow with lighter petal edge coloration.

1 Drawing Sheet

Classification: The present invention relates to a new *Rosa hybrida* plant.

Variety denomination: The new plant has the varietal denomination 'WEKsecjuc'.

BACKGROUND OF THE INVENTION

This invention relates to a new and distinct variety of Grandiflora Rose. It has as its seed parent the variety known as 'HILaroma' (U.S. Plant Pat. No. 8,494) and as its pollen parent the variety known as 'WEKvossutono' (U.S. Plant Pat. No. 18,473). It was hybridized by Christian Bédard.

SUMMARY OF THE INVENTION

Among the features which distinguish the new variety from other presently available and commercial rose cultivars known to the inventor are the following combinations of characteristics: its strong fruity to citrus-like fragrance, its red suffusion on the branches and its abundant blooms. The plant has an upright bushy moderately spreading growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKsecjuc' may be asexually propagated by cuttings, budding and grafting. The budding and grafting successfully occurred on the plant/rootstock *Rosa hybrida cv.* 'Dr. Huey' (not patented).

COMPARISON WITH PARENTS

The new rose may be distinguished from its seed parent, 'HILaroma' by the following combination of characteristics: whereas 'WEKsecjuc' bears flowers of yellow with lighter petal edge coloration with a strong fruity to citrus-like fragrance, 'HILaroma' bears flowers of cream brushed with rich pink coloration with a strong sweet and spicy fragrance. The new variety has an upright bushy moderately spreading medium height to somewhat tall growing habit (about 132 to about 178 cm. in height), whereas the seed parent has a bushy upright significantly shorter growing habit (about 120 to about 130 cm. in height).

The new variety may be distinguished from its pollen parent, 'WEKvossutono' by the following combination of characteristics: whereas 'WEKsecjuc' bears flowers of yellow with lighter petal edge coloration with a strong fruity to citrus-like fragrance, 'WEKvossutono' bears flowers of butter gold coloration with a strong licorice fragrance. The new variety has an upright bushy moderately spreading medium height to somewhat tall growing habit (about 132 to about 178 cm. in height), whereas the pollen parent has a compact and bushy significantly shorter growing habit (about 70 to about 85 cm. in height).

COMPARISON WITH THE CLOSEST COMMERCIALLY AVAILABLE CULTIVAR

The new variety may be distinguished from its closest commercially available cultivar, 'WEKsirjuci' (U.S. Plant Pat. No. 26,170) by the following combination of characteristics: whereas 'WEKsecjuc' bears double flowers (about 22 to 46 petals) of yellow with lighter petal edge coloration, 'WEKsirjuci' bears flowers of even pure yellow coloration with lesser petalage (about 24 to 33 petals). The new variety has an upright bushy moderately spreading growing habit (about 97 to about 137 cm. spread at the widest point), whereas the closest commercially available cultivar has a bushy significantly more spreading growing habit (about 150 to about 200 cm. spread at the widest point).

BRIEF DESCRIPTION OF ILLUSTRATION

The accompanying photograph illustrates the new variety and shows the flowering thereof from bud to full bloom depicted in color as nearly correct as it is possible to make in a color illustration of the character.

The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

FLOWER

The new variety sometimes bears its flowers singly, sometimes in clusters of two to four or more per stem. Flowers may be borne in regular rounded clusters on strong short to medium length stems (about 18 to about 56 cm.). The cluster ranges from about 12.5 to about 17.5 cm. in diameter. Outdoors, the plant blooms abundantly and nearly continuously during the growing season. The flowers have a strong fruity to citrus-like fragrance.

BUD

The peduncle is about 3.2 to about 8.2 cm. in length, of average to somewhat heavy caliper (about 0.2 to about 0.4 cm. in diameter), and usually erect. It is almost entirely smooth, with very few stipitate glands. Peduncle color is between 146C and 146D often moderately suffused, especially on the side exposed to the sun, with between 187B and 187A.

Before the calyx breaks, the bud is about 1.0 to about 2.1 cm. in diameter at the widest point, about 1.5 to about 2.5 cm. in length, and pointed to somewhat ovoid in shape. The surface of the bud bears between 9 to 14 foliaceous appendages with numerous hairs, usually with slender to sometimes somewhat stout entire foliaceous parts extending beyond the tip of the bud about 3/4 or more of its length. Bud color is between 137C and 146C sometimes lightly suffused, especially on the side exposed to the sun, with between 187B and 187A.

The sepals are 5 per flower, about 1.7 to about 6.1 cm. in length and about 0.6 to about 1.5 cm. in width at the widest point. The outer surface color of the sepal is between 137C and 146C sometimes lightly suffused, especially on the side exposed to the sun, with between 187B and 187A. The outer surface of the sepal is smooth and bears between 0 to 6 foliaceous appendages with numerous hairs. The inner surface color of the sepal is near 146D broadly bordered by near 137C. After the sepals open, the inner surface color is often heavily suffused, especially on the area exposed to the sun, with between 187B and 187A. The inner surface of the sepal is covered with fine wooly tomentum: sepal margins are entire and lined with few stipitate glands and numerous hairs. The sepals are moderately permanent, and usually straight in shape with acute apices.

The receptacle of the flower is of somewhat short length (about 0.2 to about 0.6 cm.) and average in caliper (about 0.6 to about 1.1 cm. in diameter). The receptacle is cup-shaped in form. Its surface is smooth with moderately thick fleshy walls. The receptacle color is between 146D and 146B.

As the petals open (after the calyx breaks), the bud is about 2.1 to about 2.9 cm. in diameter at the widest point, about 2.4 to about 3.3 cm. in length, and ovoid to somewhat pointed in form. The color of the under surfaces of the newly opened petals is between 13C and 10B. At the point where the petal attaches, there is a very small zone of between 150B and 151D. The color of the upper surfaces of the newly opened petals is between 13C and 10B. There is no visible change in coloration at the point where the petal attaches.

BLOOM

When fully open, the bloom ranges from about 8.4 to about 12.9 cm. in diameter. Petalage is double with about 22 to 46 petals and about 3 to 17 petaloids irregularly arranged. When partially open, the bloom form is somewhat high centered to cupped, and the petals are moderately tightly spiraled to cupped with petal edges somewhat reflexed outward. When fully open, the bloom form is cupped, and the petals are loosely cupped to moderately undulated with petal edges somewhat reflexed outward.

PETALS

The substance of the petals is somewhat heavy and of medium thickness, with upper surfaces somewhat satiny to slightly shiny and under surfaces moderately shiny. The petals are about 3.7 to about 5.9 cm. in length and about 2.9 to about 5.1 cm. in width at the widest point. Petal margins are entire.

The outer petals are moderately obovate to somewhat rounded in shape with rounded to sometimes mucronate apices.

The inner petals are broadly obovate in shape with rounded apices and sometimes slightly notched with one notch.

Petaloids are about 0.8 to about 4.8 cm. in length and about 0.4 to about 3.6 cm. in width at the widest point. Petaloids are irregularly shaped moderately obovate to somewhat oblanceolate to subulate with rounded to sometimes lacerated apices.

NEWLY OPENED FLOWER

The under-surface color of the outer, intermediate and inner petals is between 11B and 4B fading toward the edge of the petal with between 4C and 10D. There is no visible change in coloration at the point where the petal attaches. The upper surface color of the outer, intermediate and inner petals is between 11B and 10B fading toward the edge of the petal with between 4C and 10D. There is no visible change in coloration at the point where the petal attaches.

The under and upper surface colors of the petaloids are similar in coloration to the upper and under surfaces of the intermediate and inner petals. The general tonality of the newly opened flower is between 11B and 10B fading toward the edge of the petal with between 4C and 10D.

THREE-DAY-OLD FLOWER

The under-surface color of the outer, intermediate and inner petals is between 5D and 10D. There is no visible change in coloration at the point where the petal attaches. The upper surface color of the outer, intermediate and inner petals is between 4C and 10D. At the point where the petal attaches, there is a small zone of between 13A and 14B.

The under and upper surface colors of the petaloids are similar in coloration to the upper and under surfaces of the intermediate and inner petals.

The general tonality of the three-day-old flower is between 4C and 10D.

On the spent bloom, the petals usually drop off cleanly.

In November in Wasco, California, blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils: a few are mixed with petaloids. The filaments are of somewhat short to long length (about 0.4 to about 1.4 cm.) most with anthers. Filaments are between 12B and 13C in color. The anthers are of medium size for the class and all open approximately at the same time. Anther color when immature is near 21A on the external part and near 11C on the internal part. Anther color at maturity is near 164C on the external part and near 200A on the internal part. Pollen is abundant and near 16D in color.

FEMALE REPRODUCTIVE ORGANS

Pistils vary in number (average about 95). The styles are moderately even, average to somewhat long in length (about 0.6 to about 1.0 cm.), somewhat thin to average in caliper, and loosely bunched to somewhat separated. Stigma color is between 7C and 4A. Style color is between 1C and 2C usually moderately suffused with between 60A and 60B. Ovaries are usually all enclosed in the calyx. The ovaries are of small size and between 158B and 158A in color.

Hips are of somewhat short to average length (about 1.3 to about 2.1 cm.), somewhat cup-shaped in form with a flat top and often flat base, and between 53A and 53B in color when ripe. The hip surface is smooth with thick fleshy walls.

The seeds are irregularly rounded, smooth in texture, approximately 14 to about 26 per hip, about 0.4 to about 0.7 cm. in diameter at the widest point and between 165D and 164C in color.

FOLIAGE

The compound leaves are usually comprised of three to seven leaflets and are borne abundantly. The five-leaflet leaves are about 9.7 to about 16.8 cm. in length and about 7.0 to about 11.8 cm. in width at the widest point, moderately leathery to somewhat crisp in texture on both sides, and glossy in finish on the upper side and semi-glossy in finish on the underside. The leaves have a pinnate venation pattern. The terminal leaflets are about 4.5 to about 7.2 cm. in length and about 2.8 to about 5.0 cm. in width at the widest point, shaped ovate to somewhat oval with acute apices and rounded bases. Their margins are usually simply serrate.

The upper surface color of the mature leaf is between 139A and 147A. The under-surface color of the mature leaf is between 146A and 147C. The under and upper colors of the leaf veins on the mature leaf are similar in coloration to the upper and under surfaces colors of the mature leaf. The upper surface color of the young leaf is between 137A and 139B, usually heavily suffused with between 187B and 187A. The under-surface color of the young leaf is between 146A and 147C, usually heavily suffused with between 187B and 187A. The under and upper colors of the leaf veins on the young leaf are similar in coloration to the upper and under surfaces colors of the young leaf.

The rachis is about 2.4 to about 5.0 cm. in length, about 0.1 to about 0.2 cm in width at the widest point, and mostly rough but sometimes smooth. The upper side is deeply grooved with few hairs and stipitate glands on the edges of the grooves. The under side of the rachis is mostly rough with few stipitate glands and small prickles. The rachis color is near 146C on the under side and near 146A on the upper side, often moderately suffused on the young leaves with between 187B and 187A.

The stipules are about 1.5 to about 2.6 cm. in length and of medium width to moderately wide (about 0.5 to about 1.2 cm.) with somewhat short to medium length straight points that usually turn out at an angle of more than 45 degrees and sometimes recurve toward the stem. The under and upper surface color of the stipule is between 146A and 146B sometimes moderately suffused with between 187B and 187A. The upper and under surfaces of the stipules are smooth in texture.

The petiole is somewhat light to average in caliper and mostly rough but sometimes smooth. The upper side is deeply grooved with few hairs and stipitate glands on the edges of the grooves. The under side of the petiole is mostly rough with few stipitate glands and small prickles. The petiole is about 0.4 to about 2.4 cm. in length and about 0.1 to about 0.2 cm in width at the widest point. The petiole color is near 146C on the underside and near 146A on the upper side, often moderately suffused on the young leaves with between 187B and 187A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, California. The plant's winter hardiness and drought/heat tolerance are yet to be determined.

GROWTH

The plant has an upright bushy moderately spreading medium height to somewhat tall growing habit (about 132 to about 178 cm. in height and about 97 to about 137 cm. spread at the widest point), with full branching. It displays moderately vigorous growth and the canes are of somewhat light to medium caliper for the class (about 0.8 to about 1.5 cm. in diameter at the widest point).

The color of the major stems is between 146B and 147B. The major stems are rough in texture and they bear few large prickles that are about 0.5 to about 1.1 cm. in length. The large prickles are moderately angled to somewhat hooked downward with a moderately long somewhat narrow oval base; prickle color is between 165C and 164B sometimes lightly suffused with between 201C and 201D. The major stem bears few small prickles of similar shape and coloration.

The color of the branches is between 146C and 144A often heavily suffused with between 187B and 187A. The branches are rough in texture and they bear few large prickles which are of similar size and shape to the large prickles on the major stems; prickle color is between 152D and 152C usually heavily suffused with between 187B and 187C. The branches bear few small prickles of similar shape and coloration.

The color of the new shoots is between 146B and 146A usually heavily suffused with between 187B and 187A. The new shoots are rough in texture and they bear few large prickles which are of similar size and shape to the large prickles on the major stems; prickle color is between 152D and 152C usually heavily suffused with between 187B and 187C. The shoots bear few small prickles of similar shape and coloration.

I claim:

1. A new and distinct Grandiflora rose plant of the variety designated 'WEKsecjuc' substantially as described and illustrated herein.

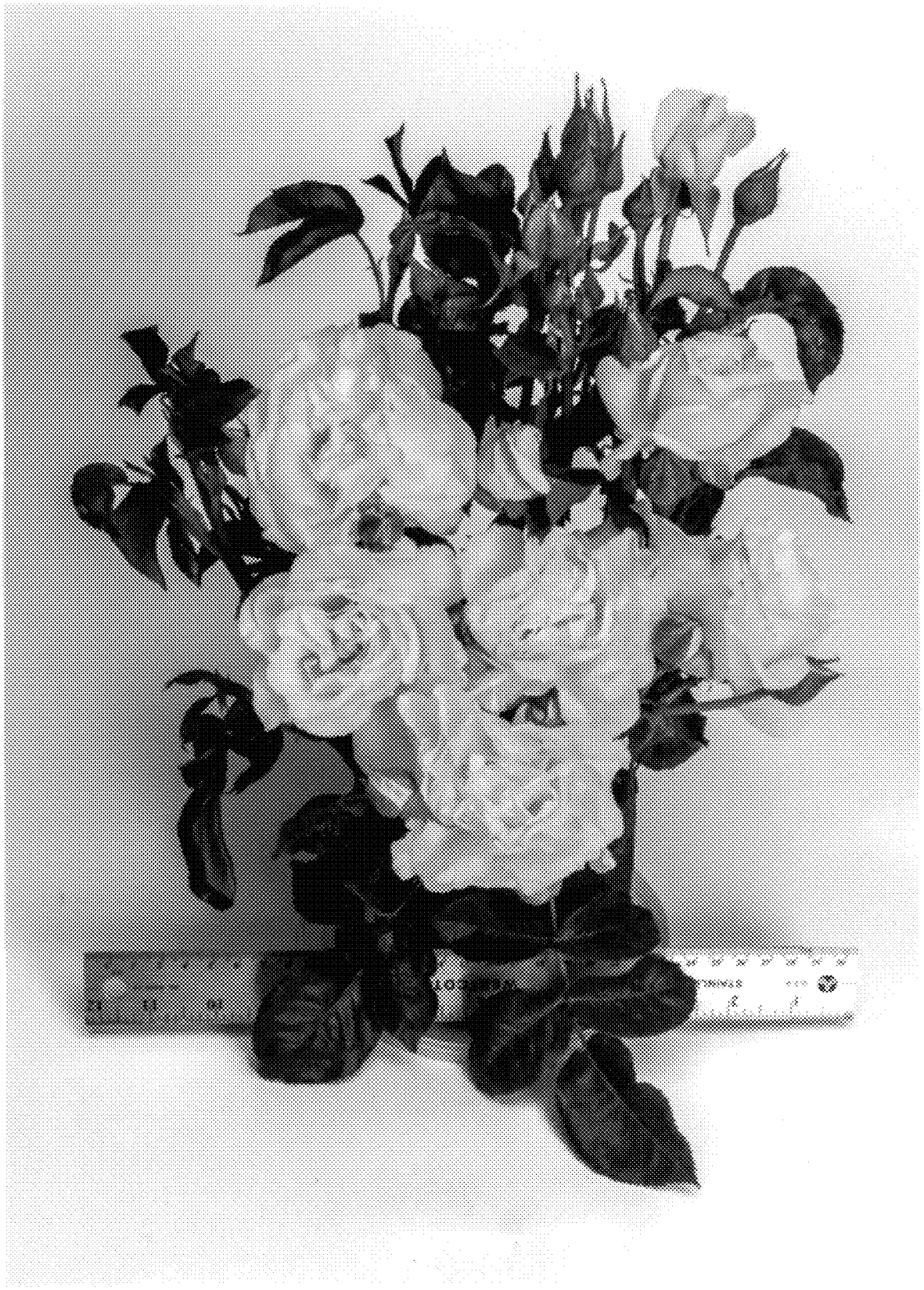

* * * * *